(12) United States Patent
Reimer et al.

(10) Patent No.: US 7,978,404 B2
(45) Date of Patent: Jul. 12, 2011

(54) SURGICAL MICROSCOPE HAVING AN OCT-SYSTEM

(75) Inventors: Peter Reimer, Ellwangen (DE); Christoph Hauger, Aalen (DE); Alfons Abele, Schwäbisch Gmünd (DE); Markus Seesselberg, Aalen (DE)

(73) Assignee: Carl Zeiss Surgical GmbH, Oberkochen (DE)

( * ) Notice: Subject to any disclaimer, the term of this patent is extended or adjusted under 35 U.S.C. 154(b) by 492 days.

(21) Appl. No.: 11/984,820

(22) Filed: Nov. 21, 2007

(65) Prior Publication Data

US 2008/0117504 A1    May 22, 2008

(30) Foreign Application Priority Data

Nov. 6, 2006  (DE) .......................... 10 2006 052 513
Apr. 24, 2007  (DE) .......................... 10 2007 019 678

(51) Int. Cl.
*G02B 21/06* (2006.01)
*G02B 21/00* (2006.01)
(52) U.S. Cl. .................. 359/385; 359/368; 359/388
(58) Field of Classification Search .......... 359/368–390, 359/618
See application file for complete search history.

(56) References Cited

U.S. PATENT DOCUMENTS

| | | | |
|---|---|---|---|
| 5,321,501 A | 6/1994 | Swanson et al. | |
| 5,493,109 A * | 2/1996 | Wei et al. | 250/201.3 |
| 5,557,453 A * | 9/1996 | Schalz et al. | 359/376 |
| 5,748,367 A * | 5/1998 | Lucke et al. | 359/385 |
| 5,795,295 A | 8/1998 | Hellmuth et al. | |
| 5,856,883 A * | 1/1999 | Sander | 359/389 |
| 6,661,572 B2 * | 12/2003 | Spink et al. | 359/372 |
| 6,819,485 B2 * | 11/2004 | Mannss | 359/388 |
| 6,862,137 B2 * | 3/2005 | Ott | 359/388 |
| 2010/0033676 A1 * | 2/2010 | De Vries et al. | 351/206 |

FOREIGN PATENT DOCUMENTS

| | | |
|---|---|---|
| DE | 10 2004 049 368 | 4/2006 |
| EP | 1 231 496 | 8/2002 |
| WO | WO 2006/100544 | 9/2006 |

OTHER PUBLICATIONS

Expanded European Search Report (Translation into English).

* cited by examiner

*Primary Examiner* — Thong Nguyen
(74) *Attorney, Agent, or Firm* — Walter Ottesen

(57) ABSTRACT

A surgical microscope (100) has a viewing beam path for main viewing and a secondary beam path (106) for viewing by another person. The surgical microscope (100) has a microscope main objective (101) through which the viewing beam path for main viewing and the viewing beam path (106) for secondary viewing pass. The surgical microscope (100) includes an OCT-system (120) for examining an object region. The OCT-system (120) includes an OCT-scanning beam (123) which is guided through the microscope main objective (101). In the viewing beam path (106) for secondary viewing, an in-coupling element (150) is provided to couple the OCT-scanning beam (123) into the viewing beam path (106) for secondary viewing and to guide the same through the microscope main objective (101) to the object region (108).

21 Claims, 5 Drawing Sheets

SURGICAL MICROSCOPE HAVING AN OCT-SYSTEM

CROSS REFERENCE TO RELATED APPLICATION

This application claims priority of German patent application no. 10 2007 019 678.6, filed Apr. 24, 2007, the entire content of which is incorporated herein by reference.

FIELD OF THE INVENTION

The invention relates to a surgical microscope having a viewing beam path and a microscope main objective through which the viewing beam path passes.

BACKGROUND OF THE INVENTION

A surgical microscope of the kind referred to above is known from German patent publication 10 2004 049 368 A1. Here, a surgical microscope is described having a binocular tube for main viewing and a binocular tube for secondary viewing. The binocular tube for main viewing and the binocular tube for secondary viewing are mounted on a common surgical microscope base body. The binocular tube for main viewing and the binocular tube for secondary viewing have stereoscopic viewing beam paths. These viewing beam paths pass through a common microscope main objective.

A surgical microscope which includes an OCT-system is described in U.S. Pat. No. 5,795,295.

An OCT-system (Optical Coherence Tomography) permits the non-invasive illustration and measurement of structures within a tissue utilizing optical coherence tomography. As an image providing process, the optical coherence tomography permits especially section images or volume images of biological tissue to be generated with micrometer resolution. A corresponding OCT-system includes a source for time-dependent incoherent and spatially coherent light having a specific coherence length which is guided to a specimen beam path and a reference beam path. The specimen beam path is directed onto the tissue to be examined. Laser radiation, which is radiated back into the specimen beam path because of scatter centers in the tissue, superposes the OCT-system with laser radiation from the reference beam path. An interference signal develops because of the superposition. The position of the scatter centers for the laser radiation in the examined tissue can be determined from this interference signal.

For OCT-systems, the building principles of the "time-domain OCT" and of the "Fourier-domain OCT" are known.

The configuration of a "time-domain OCT" is described, for example, in U.S. Pat. No. 5,321,501 with reference to FIG. 1a at column 5, line 40, to column 11, line 10. In a system of this kind, the optical path length of the reference beam path is continuously varied via a rapidly moving reference mirror. The light from specimen beam path and reference beam path is superposed on a photo detector. When the optical path lengths of the specimen and reference beam paths are coincident, then an interference signal is provided on the photo detector.

A "Fourier-domain OCT" is, for example, described in international patent publication WO 2006/100544 A1. To measure the optical path length of a specimen beam path, light from a reference beam path is superposed onto light from the specimen beam path. In contrast to the time-domain OCT, the light from the specimen beam path and reference beam path is not supplied directly to a detector for a measurement of the optical path length of the specimen beam path but is first spectrally dispersed by means of a spectrometer. The spectral intensity of the superposed signal generated in this manner from specimen beam path and reference beam path is then detected by a detector. By evaluating the detector signal, the optical path length of the specimen beam path can be determined.

The OCT-system of the surgical microscope disclosed in U.S. Pat. No. 5,795,295 contains a component assembly for generating an OCT-scanning beam of short coherent laser radiation and having an analyzing unit for evaluating interference signals. A unit for scanning the OCT-scanning beam is assigned to this component assembly. The unit for scanning includes two scanning mirrors to scan a surgical region with the OCT-scanning beam. The two mirrors can be displaced about two movement axes. In the surgical microscope of U.S. Pat. No. 5,795,295, the OCT-scanning beam is coupled into the illuminating beam path of the surgical microscope via a divider mirror and the OCT-scanning beam is directed with this illuminating beam through the microscope main objective to the object region.

SUMMARY OF THE INVENTION

It is an object of the invention to detect depth images of an object region.

The surgical microscope of the invention is for defining a viewing beam path. The surgical microscope comprises: a microscope main objective mounted so as to permit the viewing beam path to pass therethrough; an OCT-system for examining a region of an object; the OCT-system providing an OCT-scanning beam guided through the microscope main objective; and, an in-coupling element mounted in the viewing beam path for coupling the scanning beam into the viewing beam path and for guiding the scanning beam through the microscope main objective to the region of the object.

In this way, it is possible to integrate an OCT-system into a surgical microscope without optical beam paths being vignetted in the surgical microscope and without image cropping occurring as a consequence thereof.

According to another embodiment of the invention, the in-coupling element is configured as a divider mirror, especially as a planar mirror or splitter cube. In this way, a secondary viewer always has a clear view of the object region.

According to another feature of the invention, the surgical microscope includes a viewing beam path for primary viewing and a viewing beam path for secondary viewing with these beam paths passing through the microscope main objective. The in-coupling element is mounted in the viewing beam path for secondary viewing.

According to another feature of the invention, an optical assembly is arranged in the viewing beam path for secondary viewing in order to transpose a parallel viewing beam into an intermediate image. The in-coupling element in the viewing beam path for secondary viewing is mounted between the optical assembly and the microscope main objective. However, the in-coupling element can also be provided between the optical assembly and the intermediate image.

According to another feature of the invention, the OCT-system for scanning the OCT-scanning beam includes a first scan mirror. Preferably, a second scan mirror is provided. The first scan mirror can be moved about a first rotational axis and the second scan mirror can be moved about a second rotational axis. The first and second rotational axes are offset laterally with respect to each other at right angles. In this way, a scanning of an object region is possible in correspondence to a perpendicularly running raster pattern.

In another embodiment of the invention, the OCT-system includes a light conductor which has a light exit portion for the OCT-scanning beam. Means for moving the light exit portion of the light conductor are provided. In this way, an OCT-scanning plane can be varied in the object region and it is possible to adjust the system for different OCT-wavelengths considering the optical components in the viewing beam path for secondary viewing. These optical components are designed for visible light.

In a further embodiment of the invention, an adjustable optical element is provided in the OCT-scanning beam path for the adjustment of a geometric image of the exit end face of a light conductor in an OCT-scanning plane. In this way, the OCT-scanning plane of the surgical microscope can be displaced relative to the viewing plane of the optical viewing beam paths of the system.

According to another feature of the invention, a drive unit is assigned to the adjustable optical element. In this way, the OCT-scanning plane can, for example, be varied by a pregiven amount relative to the viewing plane of the surgical microscope.

According to another feature of the invention, the OCT-system is designed for making available a first OCT-scanning light beam with a first wavelength and for making available a second OCT-scanning light beam with a second wavelength different from the first wavelength. In this way, the surgical microscope can be optimized for the examination of different tissue structures and body organs of a patient.

According to another feature of the invention, first and second OCT-systems are provided which make available OCT-scanning light beams of different wavelengths. In this way, an examination of an object region is possible on the basis of different OCT-wavelengths with maximum resolution.

According to another feature of the invention, the OCT-scanning light beam of the first OCT-system is at least partially superposed onto a right stereoscopic viewing beam and the OCT-scanning light beam of the second OCT-system is at least partially superposed onto a left stereoscopic viewing beam. The microscope main objective is passed through in different regions thereof by the beam paths. Preferably, the first OCT-system makes available an OCT-scanning light beam having the wavelength $\lambda_1=1300$ nm and the second OCT-system makes available an OCT-scanning light beam having the wavelength $\lambda_2=800$ nm. In this way, the layer configuration of the cornea and the structure of the retina can be examined simultaneously with the surgical microscope on an eye of a patient.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
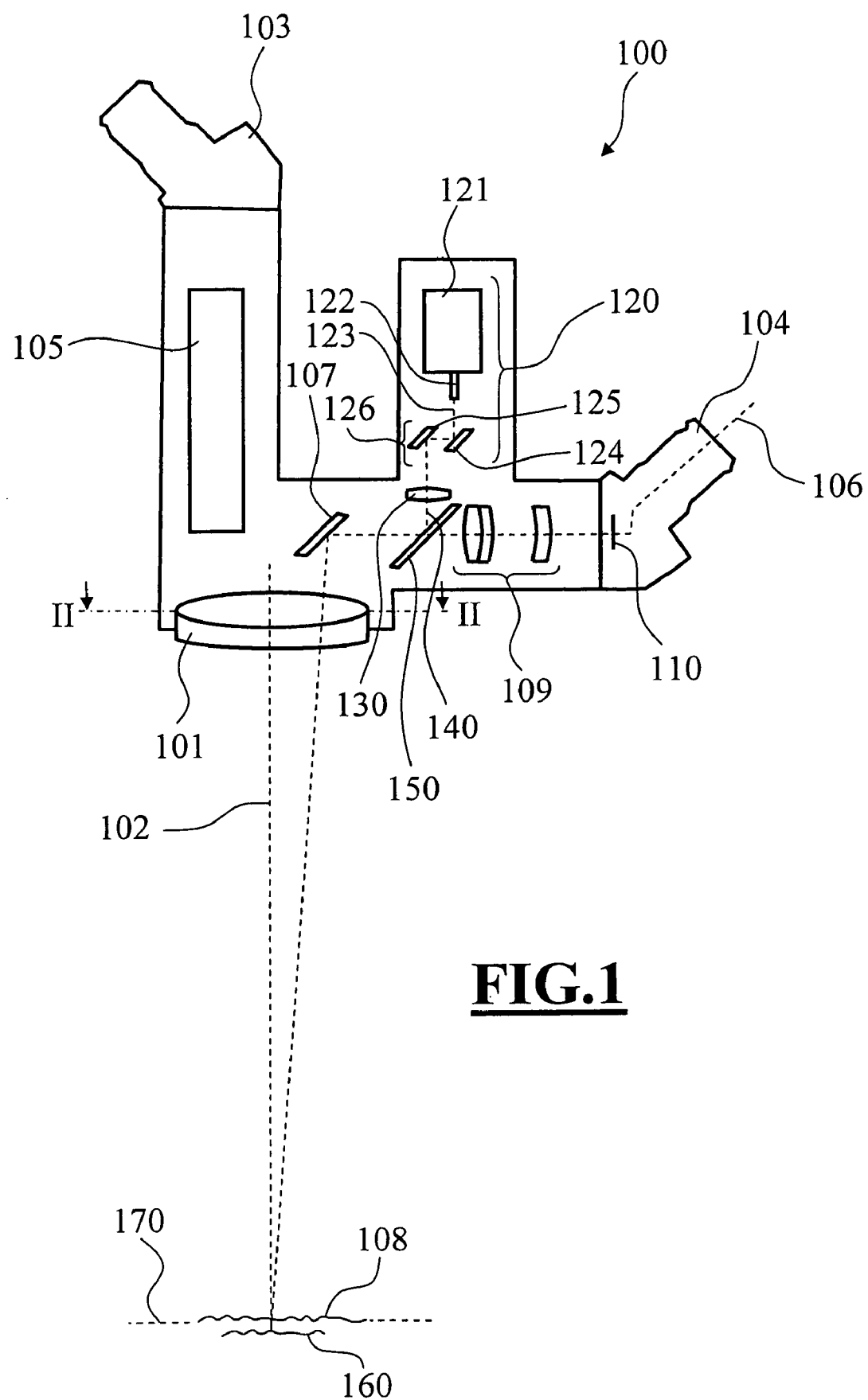
FIG. 1 shows a first surgical microscope having an integrated OCT-system.

The surgical microscope 100 in FIG. 1 has a microscope main objective 101 having an optical axis 102. The microscope main objective 101 has a focal plane 170 and stereoscopic viewing beam paths of a binocular tube 103 for primary viewing and of a binocular tube 104 for secondary viewing pass through this microscope main objective. A zoomable magnification system 105 is assigned to the binocular tube 103 for primary viewing. FIG. 1 shows the right viewing beam path 106 of the stereoscopic viewing beam path from the binocular tube for secondary viewing. This viewing beam path is deflected to the object region 108 by a path-folding mirror 107 which is mounted on the side of the microscope main objective 101 facing away from the object region 108. A lens system 109 is disposed in the viewing beam path 106. The lens system 109 bundles the viewing beam path 106 to an intermediate image 110 in the binocular tube 104 for secondary viewing. The viewing beam path 106 passes through the microscope main objective and is parallel after passing through the microscope main objective 101.

The surgical microscope 100 contains an OCT-system 120 for recording OCT images. This OCT-system includes a unit 121 for generating and analyzing an OCT-scanning beam path. The unit 121 is integrated into the surgical microscope 100. The unit can, however, be mounted outside of the surgical microscope, for example, in a console of a stand. The unit 121 is connected to a light conductor 122. The unit 121 makes an OCT-scanning beam path available via this light conductor 122. The scanning beam 123 exiting from the light conductor 122 is guided to a first scanning mirror 124 and a second scanning mirror 125 of an OCT-scanning unit 126. The scanning beam 123 passes through a converging lens 130 downstream of the OCT-scanning unit 126. The converging lens 130 bundles the scanning beam 123 to a bundle 140 of parallel rays.

It is also possible to deflect a parallel OCT-scanning beam path with the first scanning mirror 124 and the second scanning mirror 125 of the OCT-scanning unit 126. For this purpose, a suitable converging lens (not shown in FIG. 1) is mounted between light conductor 122 and OCT-scanning unit 126. The converging lens 130, which is disposed on the side of the OCT-scanning unit 126 which faces away from the light conductor, is then not necessary. The beam 140 from the OCT-scanning unit 126 is guided to a divider mirror 150. The divider mirror 150 is mounted in the viewing beam path 106. The divider mirror 150 is essentially transparent for the spectral range of viewing light in this viewing beam path. This spectral range is visible for persons. The divider mirror 150, however, reflects the OCT-scanning beam path and superposes the same onto the viewing beam path 106. The divider mirror 150 can be configured as a mirror element having planar plates but also as a divider cube.

The light of the OCT-scanning beam 123 is bundled by the microscope main objective 101 in an OCT-scanning plane 160. The OCT-scanning plane 160 is the plane of the geometric image of the exit end of the light conductor 122 into the object region. This geometric image is determined via the optical elements in the OCT-scanning beam path with OCT-scanning unit 126, converging lens 130, divider mirror 150, path-folding mirror 107 and microscope main objective 101. Stated otherwise, the corresponding geometric image of the light conductor exit end lies in the OCT-scanning plane 160.

The light backscattered into the OCT-scanning beam path arrives back in the unit 121 via the path-folding mirror 107 and the divider mirror 150. There, the OCT-scanning light, which is backscattered from the object region, interferes with the OCT-beam from a reference beam path. The interference signal is detected by a detector and is evaluated by a computer unit which, from this signal, determines an optical path length difference between scatter centers for OCT-light in the object region and the path length of light in the reference branch.

Figure 2:
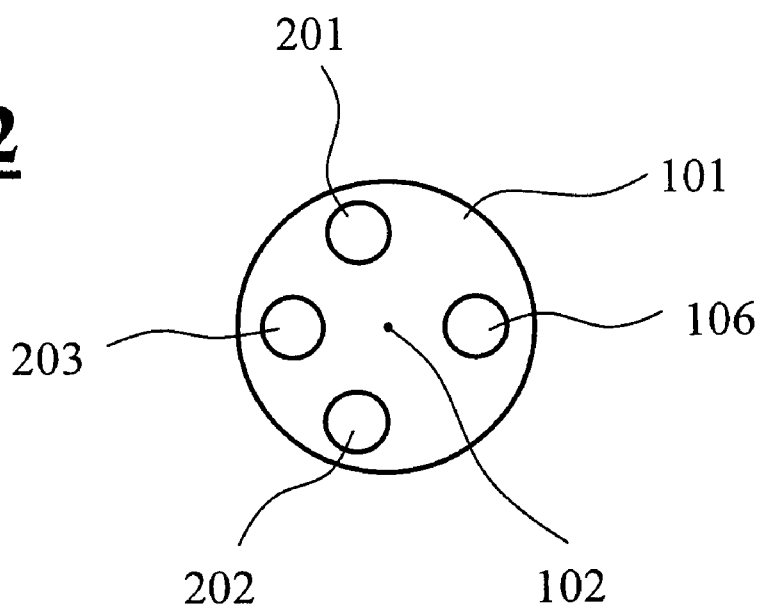
FIG. 2 shows a section of the microscope main objective along the line II-II of FIG. 1.

FIG. 2 is a section taken along line II-II of FIG. 1. FIG. 2 explains the course of the stereoscopic viewing beam paths from binocular tube 103 and binocular tube 104 of the surgical microscope 100 of FIG. 1. The optical axis 102 of the microscope main objective 101 lies at the center thereof. The stereoscopic beam path for primary viewing (201, 202) and the stereoscopic beam path for secondary viewing (203, 106) pass through the microscope main objective 101 in sectional regions separated from each other.

Figure 3:
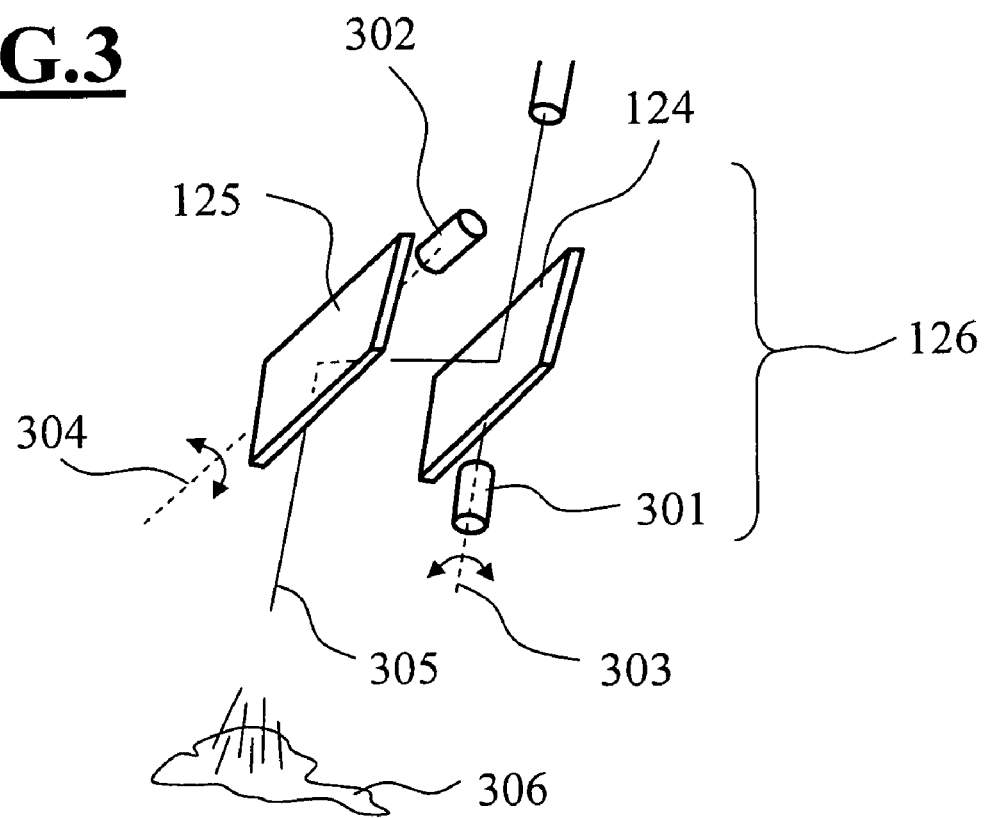
FIG. 3 shows a portion of the OCT-system in the surgical microscope.

FIG. 3 shows the OCT-scanning unit 126 of the surgical microscope 100 of FIG. 1. The first scan mirror 124 and the second scan mirror 125 are arranged to be rotatably movable via positioning drives (301, 302) about two mutually perpendicular axes (303, 304). This permits the OCT-scanning beam path 305 to scan over a plane 306.

Figure 4:
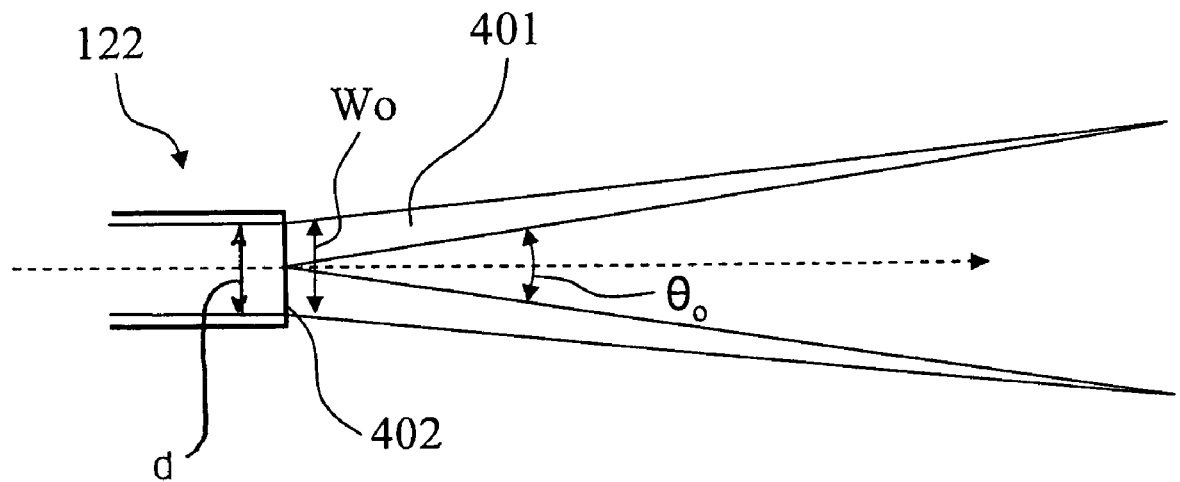
FIG. 4 shows an intensity distribution of the OCT-scanning light beam exiting from the light conductor of the OCT-system in the surgical microscope.

FIG. 4 shows a front portion of the light conductor 122 having front face 402. The light conductor 122 operates as a monomode fiber for light of the wavelength $\lambda$=1310 nm. The diameter (d) of the fiber core of the light conductor 122 satisfies the relationship:

$$\frac{d}{2} < 2.4 \frac{\lambda}{2\pi NA},$$

wherein: NA is the numerical aperture of the front face of the light conductor. Preferably, the diameter (d). of the fiber core of the light conductor 122 lies in the range of 5 µm<d<10 µm. In this parameter range, the light conductor 122 conducts the light with a Gaussian-shaped wave mode. The OCT-scanning light beam 401 exits from the light conductor 122 with an approximately Gaussian-shaped beam profile which is characterized by a waist parameter $W_0$ and an aperture parameter $\theta_0$ wherein:

$$\theta_0 = \frac{2\lambda}{\pi W_0}$$

An aperture angle of $\theta_0 \approx 0.0827$ rad results thereby as an index for the beam divergence for a fiber core diameter of $d_0$=10 µm and a wavelength $\lambda_0$=1310 nm.

The front face 402 of the light conductor 122 is imaged on the object region 108 in the OCT-scanning plane 160 via the following: the scan mirrors 124 and 125 in the surgical microscope 100 of FIG. 1; the converging lens 130; the divider mirror 150; the path-folding mirror 107; and, the microscope main objective 101.

Figure 5:
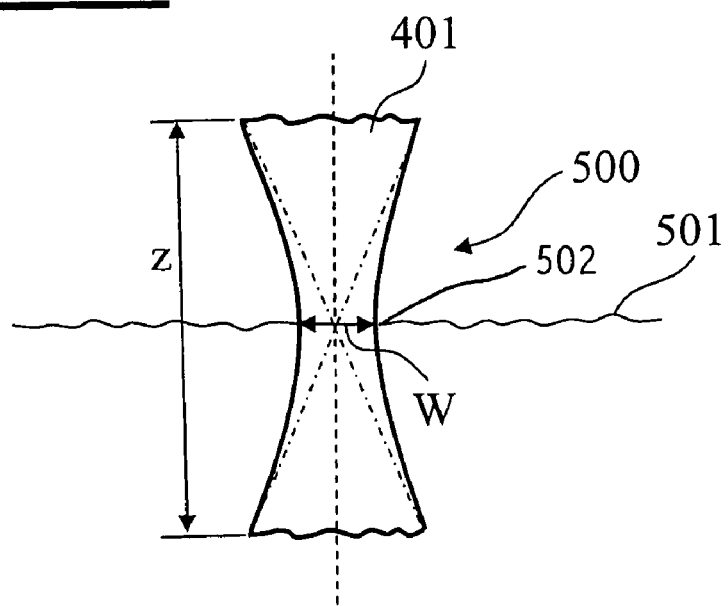
FIG. 5 shows an intensity distribution of the OCT-scanning beam in the OCT-scanning plane in the object region of the surgical microscope.

FIG. 5 shows the course of the intensity distribution of the OCT-scanning light beam 401 perpendicular to the OCT-scanning plane 501. In the OCT-scanning plane 501, the intensity distribution of the OCT-scanning radiation has a smallest waist. The diameter of the OCT-scanning beam path increases outside of the OCT-scanning plane. The OCT-scanning light beam 401 exits from the light conductor 122 of FIG. 4 with an approximately Gaussian-shaped beam profile. For this reason, the converging lens 130 and the microscope main objective 101 effect a so-called Gaussian bundle 500 of the OCT-scanning light beam 401 in the region of the OCT-scanning plane 160. This Gaussian bundle 500 is characterized by the confocal parameter (z) as an index for the longitudinal expansion of the waist of the Gaussian bundle and by the waist parameter W as an index for the diameter of the smallest constriction 502 of the OCT-scanning light beam 401, that is, for the diameter of the waist thereof. The following applies:

$$z = 2 \frac{W^2 \pi}{\lambda},$$

wherein: $\lambda$ is the wavelength of the OCT-scanning light beam. The following relationship applies between the waist parameter W of the Gaussian bundle 500 and the waist parameter $W_0$ of the scanning light beam 401 (FIG. 4) which exits from the light conductor 122:

$$W = \beta W_0,$$

wherein: $\beta$ is the magnification parameter or demagnification parameter of the above-mentioned geometric image of the exit end of light conductor 122 of FIG. 1 in the OCT-scanning plane. The parameter $\beta$ is coupled to the focal length $f_1$ of the converging lens 130 of FIG. 1 and the focal length $f_2$ of the microscope main objective via the following relationship:

$$\frac{f_2}{f_1} = \beta$$

The size of structures, which can be resolved with the OCT-scanning light beam 401, is determined by the diameter of the beam 401 in the OCT-scanning plane 160, that is, by the waist parameter W. If, for example, an application requires a lateral resolution of the OCT-system in the surgical microscope of approximately 40 µm, then, according to the Nyquist theorem, the cross section of the OCT-scanning light beam 401 must amount to approximately 20 µm on the surface. For a given wavelength $\lambda$ for the OCT-scanning light beam 123 of FIG. 1, the magnification of the optical image in the OCT-beam path and the diameter of the fiber core in the light conductor 122 must be suitably selected for a desired resolution of the OCT-system 120.

The confocal parameter (z) as an index for the longitudinal expansion of the waist of the Gaussian bundle determines the axial depth of field from which backscattered light can be detected in the OCT-scanning beam path 123 of FIG. 1. The smaller the confocal parameter (z), the greater is the loss of the OCT-system with respect to lateral resolution when removing an object from the OCT-scanning plane 160 with this object having been scanned with the OCT-scanning beam. The reason for this is that the location of the scatter centers can be localized only within the "funnel" defined by the waist parameter W and the confocal parameter (z).

As the axial resolution of an OCT-system is delimited on the one hand by the specific coherence length of the light of the light source utilized in the OCT-system and, on the other hand, the lateral resolution of the OCT-system decreases when the depth index thereof exceeds the expansion given by the confocal parameter (z), then the adjustment of the confocal parameter (z) to the depth index of the OCT-system is favorable. The depth index is a measuring range within which scattering centers in the object can be measured in the z-direction.

For a specific wavelength λ of the OCT-scanning light beam 401, the possible lateral resolution of the OCT-system of FIG. 1 results because the wavelength λ and confocal parameter (z) determine the waist parameter W. The optical units in the OCT-scanning beam path 123 of FIG. 1 and the dimensioning of the fiber core of the light conductor 122 are then to be selected so that the particular waist parameter W results.

The surgical microscope 100 is so designed that the focal plane 170 of the microscope main objective 101 for the visible spectral region and the OCT-scanning plane 160 are coincident. Then, the waist 502 of the OCT-scanning light beam shown in FIG. 5 lies in the focus plane of the surgical microscope.

Alternative to this design of the surgical microscope, an offset of the OCT-scanning plane and the focus plane of the surgical microscope can be provided. Preferably, this offset is not greater than the confocal parameter (z) of the OCT-scanning light beam in the region of the OCT-scanning plane. This makes it possible, for example, to visualize an object region utilizing OCT with this object region lying directly below the focus plane of the surgical microscope. However, it can also be purposeful to provide for a specific application a defined offset which exceeds the confocal parameter in order, for example, to examine the front side of the cornea of the eye of a patient with the surgical microscope and, at the same time, to visualize the rear side of the cornea of the patient eye or the lens thereof by means of the OCT-system.

Figure 6:
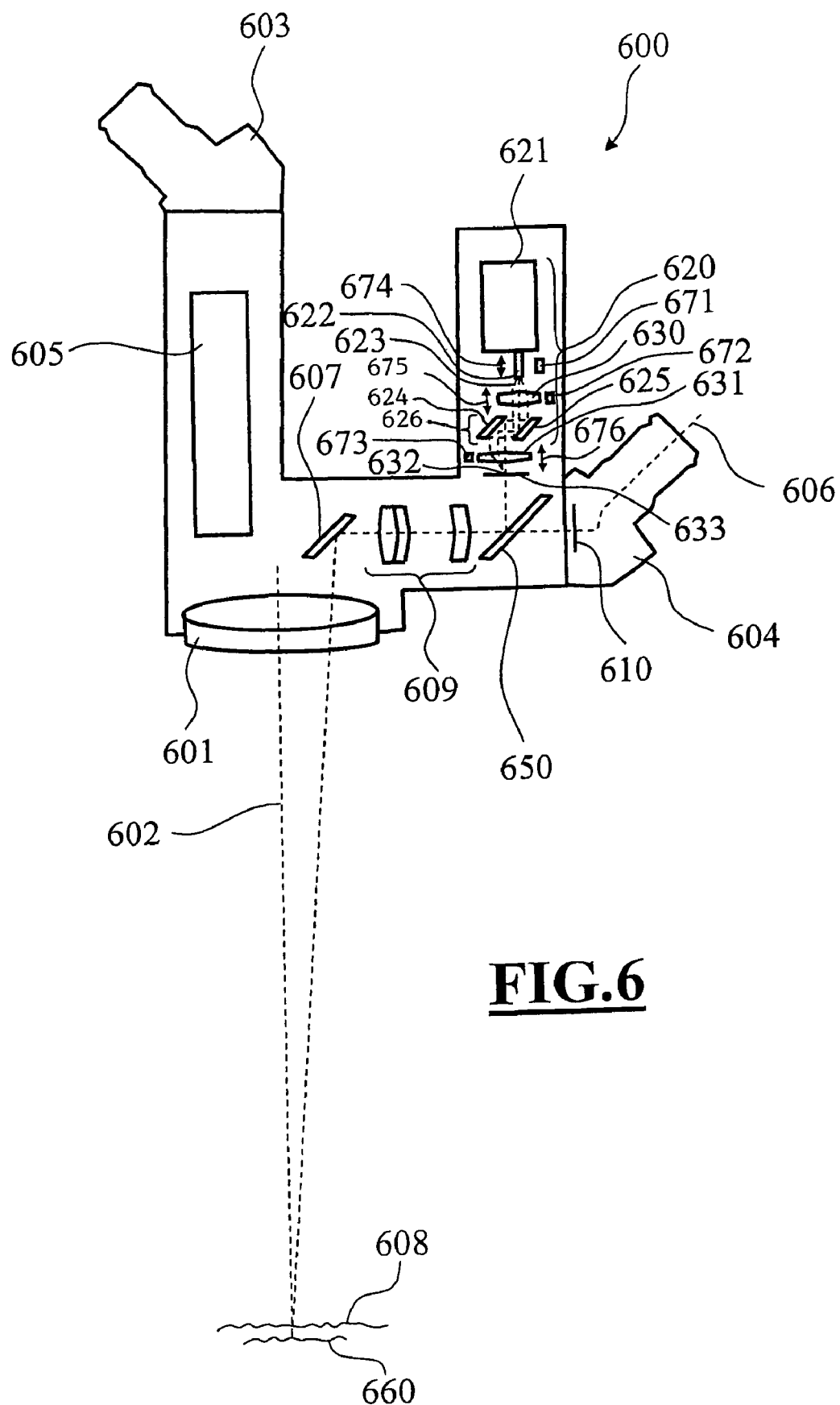
FIG. 6 shows a second surgical microscope having an integrated OCT-system.

FIG. 6 shows a further surgical microscope 600 having an integrated OCT-system 620. Insofar as the component assemblies of the surgical microscope 600 correspond to the component assemblies of the surgical microscope 100 of FIG. 1, the component assemblies in FIG. 6 have the same reference numerals increased by the number 500.

The surgical microscope 600 differs from the surgical microscope 100 of FIG. 1 in that a divider mirror 650 is provided which is disposed in the convergent viewing beam path between a tube lens system 609 and an intermediate image 610 of the object region generated thereby. The OCT-system 620 includes a unit 621 for the generation of an OCT-scanning beam 623 in two different wavelength ranges. It generates an OCT-scanning light beam having a wavelength λ=800 nm and an OCT-scanning light beam having a wavelength λ=1310 nm.

The OCT-scanning beam 623, which exits from the light conductor 622, is directed via a first OCT-lens system 630 onto the scanning mirror unit 626 having scan mirrors (624, 625). The scanning beam 623 reaches a second OCT-lens system 631 from the scanning mirror unit 626. The OCT-lens system (630, 631) effects an intermediate image 632 of the light conductor exit end face in a plane 633 which is conjugated to the OCT-scanning plane 660 in the object region 608.

In order to permit an operator to adjust the OCT-scanning plane 660 with reference to the object plane 608 of the optical viewing beam paths in the surgical microscope 600, an adjustability of the lens systems (630, 631) and of the exit end of the light conductor 622 is provided. For this purpose, the surgical microscope 600 includes drive units (671, 672, 673) which are assigned to the lens systems (630, 631) and the light conductor 622. With these drive units (671, 672, 673), the lens systems (630, 631) and the light conductor 622 can be displaced corresponding to the double arrows (674, 675, 676). Especially, not only can the position of the OCT-scanning plane 660 be varied but a magnification or demagnification of the exit end of the light conductor 622 can be adjusted to a desired value.

A modified embodiment of the surgical microscope 600 shown in FIG. 6 includes a focusable microscope main objective having an adjustable focal length. This measure too permits the displacement of an OCT-scanning plane and the change of the geometric imaging of the light conductor exit end face in the OCT-scanning plane.

With a displacement of the OCT-scanning plane of the OCT-system 620 in the surgical microscope 600, the reference beam path of the system (not shown here) is preferably readjusted so that this reference beam path always is adapted to the adjusted OCT-scanning plane.

Figure 7:
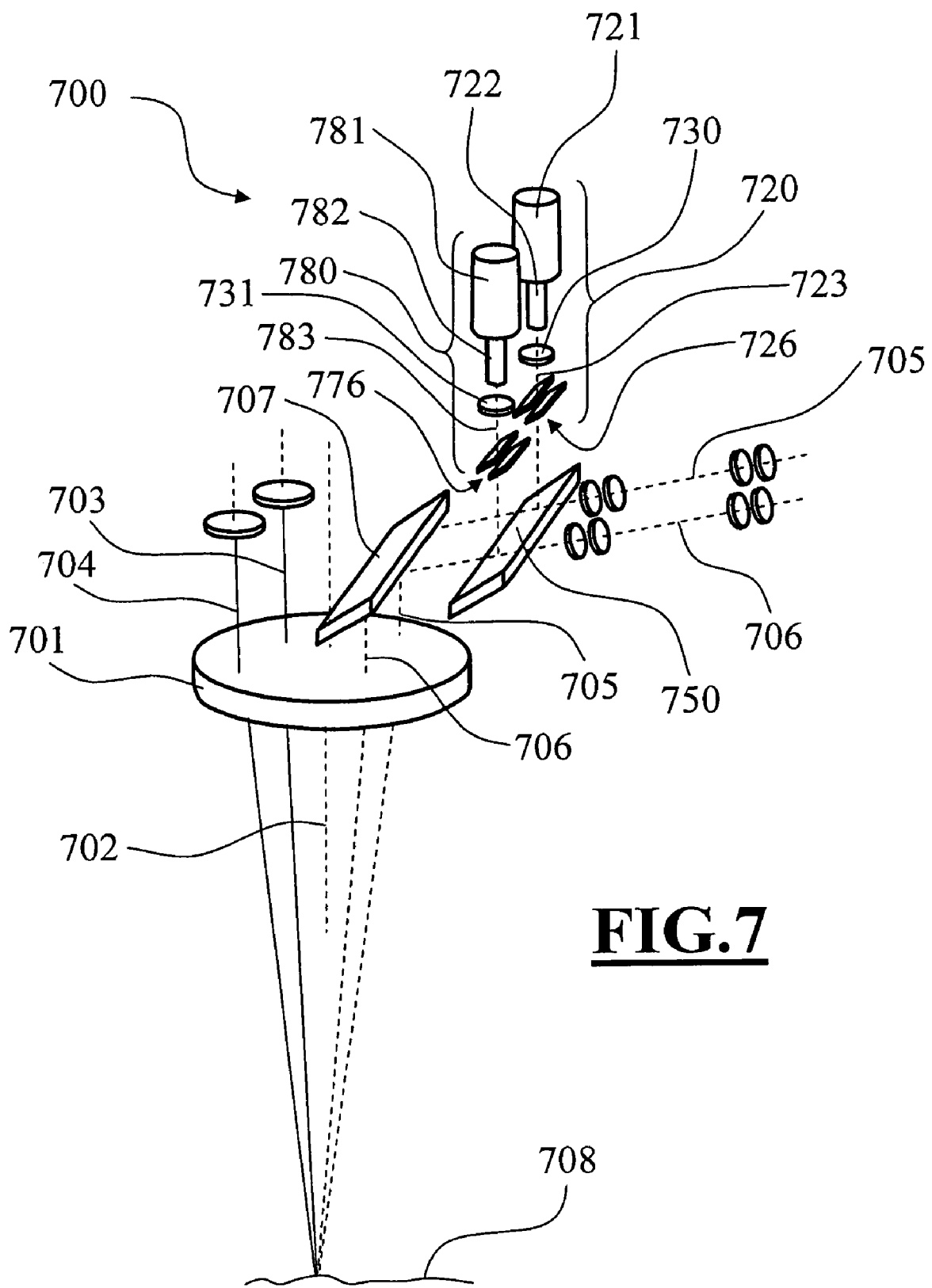
FIG. 7 shows a portion of a third surgical microscope having two integrated OCT-systems.

FIG. 7 shows a section of a third surgical microscope 700 wherein two OCT-systems (720, 780) are provided. The surgical microscope has a microscope main objective 701 defining an optical axis 702. A left and a right stereoscopic viewing beam path (703, 704) for the main viewing and a left and right stereoscopic viewing beam path (705, 706) for secondary viewing pass through the objective 701. The stereoscopic viewing beam paths (705, 706) for the secondary viewing are directed by the path-folding mirror 707 to the object region 708. The path-folding mirror 707 is mounted on the side of the microscope main objective 701 facing away from the object region 708.

The OCT-systems (720, 780) each include a unit (721, 781) for generating and analyzing an OCT-scanning beams. These units (721, 781) provide, via light conductors (722, 782), a first OCT-scanning beam 723 and a second OCT-scanning beam 783 having respective wavelengths ($\lambda_1, \lambda_2$). The OCT-scanning beams (723, 783) are directed via converging lenses (730, 731) and scanning mirrors of OCT-scanning units (726, 776) to a divider mirror 750.

The divider mirror 750 is mounted in the stereoscopic viewing beam path for the secondary viewing (705, 706). The divider mirror is essentially transparent for the spectral range of viewing light visible for humans but reflects the OCT-scanning beams (723, 783) in such a manner that these scanning beams are superposed onto the viewing beam paths (705, 706) and pass therewith through the microscope main objective 701.

The light which is radiated back into the OCT-scanning beam paths (723, 783) from the object region 708 is evaluated in the units (721, 781) for the generation and analysis of the particular OCT-scanning beam.

The use of two OCT-systems permits an object region to be scanned with OCT-light of different wavelengths. For each one of the OCT-scanning beams, a selection, which is optimal for maximum resolution, can be made from: wavelengths ($\lambda_1, \lambda_2$) the confocal parameters ($z_1, z_2$); and, the waist parameters ($W_1, W_2$).

It is understood that the foregoing description is that of the preferred embodiments of the invention and that various changes and modifications may be made thereto without departing from the spirit and scope of the invention as defined in the appended claims.

What is claimed is:

1. A surgical microscope defining a viewing beam path and comprising:
   a microscope main objective mounted so as to permit said viewing beam path to pass therethrough;
   an OCT-system for examining a region of an object;
   said OCT-system providing an OCT-scanning beam guided through said microscope main objective; and,
   an in-coupling element mounted in said viewing beam path for coupling said OCT-scanning beam into said viewing beam path so as to superpose said OCT-scanning beam onto said viewing beam path and for guiding said OCT-scanning beam through said microscope main objective to said region of said object.

2. The surgical microscope of claim 1, wherein said in-coupling element is a divider mirror.

3. The surgical microscope of claim 2, wherein said divider mirror is a planar mirror.

4. The surgical microscope of claim 1, wherein said in-coupling element is a divider cube.

5. The surgical microscope of claim 1, wherein said OCT-scanning beam is a first OCT-scanning beam; said OCT-system comprises a first scanning mirror for scanning said first OCT-scanning beam; and, a first device for rotating said first mirror about a first rotational axis.

6. The surgical microscope of claim 5, wherein said OCT-system provides a second OCT-scanning beam; said OCT-system further comprises a second scanning mirror for scanning said second OCT-scanning beam; and, a second device for rotating said second mirror about a second rotational axis laterally offset at A right angle to said first rotational axis.

7. The surgical microscope of claim 1, wherein said OCT-system further comprises a light conductor having an end portion having a light exit end face for said OCT-scanning beam whereat said OCT-scanning beam exits from said light conductor with an approximately Gaussian-shaped beam profile; and, means for moving said end portion.

8. The surgical microscope of claim 7, wherein said OCT-system further comprises an adjustable optical element mounted in the path of said OCT-scanning beam for adjusting a geometric image of said exit end face of said light conductor.

9. The surgical microscope of claim 8, wherein said OCT-system further comprises a drive unit assigned to said adjustable optical element.

10. The surgical microscope of claim 1, wherein said OCT-scanning beam is a first OCT-scanning beam; said OCT-system provides a second OCT-scanning beam; and, said first OCT-scanning beam has a first wavelength and said second OCT-scanning beam has a second wavelength.

11. The surgical microscope of claim 1, wherein said OCT-system is a first OCT-system providing a first OCT-scanning beam and said surgical microscope further comprises a second OCT-system providing a second OCT-scanning beam; and, said first and second OCT-scanning beams have different wavelengths.

12. The surgical microscope of claim 1, wherein said in-coupling element is a divider mirror for reflecting said OCT-scanning beam into said viewing beam path.

13. The surgical microscope of claim 1, wherein said viewing beam path and said OCT-scanning beam superposed onto said viewing beam path pass through said microscope main objective at the same location on said microscope main objective.

14. The surgical microscope of claim 1, wherein said OCT-system further comprises a light conductor having an end portion having a light exit end face for said OCT-scanning beam whereat said OCT-scanning beam exits from said light conductor with an approximately Gaussian-shaped beam profile; and, means for moving said end portion so that an OCT-scanning plane of the surgical microscope is displaced relative to a viewing plane of said optical viewing beam path.

15. A surgical microscope defining a viewing beam path and comprising:

a microscope main objective mounted so as to permit said viewing beam path to pass therethrough;
an OCT-system for examining a region of an object;
said OCT-system providing an OCT-scanning beam guided through said microscope main objective;
an in-coupling element mounted in said viewing beam path for coupling said OCT-scanning beam into said viewing beam loath and for guiding said OCT-scanning beam through said microscope main objective to said region of said object;
said OCT-system being a first OCT-system providing a first OCT-scanning beam and said surgical microscope further comprising a second OCT-system providing a second OCT-scanning beam; and, said first and second OCT-scanning beams having different wavelengths;
said viewing beam path being a right stereoscopic viewing beam path and said surgical microscope defining a left stereoscopic viewing beam path;
said first OCT-scanning beam being at least partially superposed onto said right stereoscopic viewing beam path so as to pass therewith through said microscope main objective; and, said second OCT-scanning beam being at least partially superposed onto said left stereoscopic viewing beam path so as to pass through said microscope main objective therewith.

16. The surgical microscope of claim 15, wherein said first OCT-system provides said first OCT-scanning beam at a wavelength of $\lambda_1$=1300 nm and said second OCT-system provides said second OCT-scanning beam at a wavelength of $\lambda_2$=800 nm.

17. A surgical microscope defining a primary viewing beam path for viewing by a first viewer and a secondary viewing beam path for viewing by a second viewer and comprising:

a microscope main objective mounted so as to permit said first and second viewing beam paths to pass therethrough;
an OCT-system for examining a region of an object;
said OCT-system providing an OCT-scanning beam guided through said microscope main objective; and,
an in-coupling element mounted in said second viewing beam path for coupling said OCT-scanning beam into said second viewing beam path so as to superpose said OCT-scanning beam onto said second viewing beam path and for guiding said OCT-scanning beam through said microscope main objective to said region of said object.

18. The surgical microscope of claim 17, further comprising an optical assembly mounted in said secondary viewing beam path for transposing a parallel secondary viewing beam into an intermediate image.

19. The surgical microscope of claim 18, wherein said in-coupling element is mounted between said optical assembly and said microscope main objective.

20. The surgical microscope of claim 18, wherein said in-coupling element is mounted between said optical assembly and said intermediate image.

21. The surgical microscope of claim 17, wherein said in-coupling element is a divider mirror for reflecting said OCT-scanning beam into said second viewing beam path.

* * * * *

UNITED STATES PATENT AND TRADEMARK OFFICE
CERTIFICATE OF CORRECTION

| | |
|---|---|
| PATENT NO. | : 7,978,404 B2 |
| APPLICATION NO. | : 11/984820 |
| DATED | : July 12, 2011 |
| INVENTOR(S) | : Peter Reimer et al. |

It is certified that error appears in the above-identified patent and that said Letters Patent is hereby corrected as shown below:

Title Page:
Under (30) Foreign Application Priority Data: delete "Nov. 6, 2006 (DE) ............ 10 2006 052 513".

Column 8:
Line 48: delete "$\lambda_2$)" and substitute -- $\lambda_2$); -- therefor.

Column 9:
Line 19: delete "A" and substitute -- a -- therefor.

Column 10:
Line 8: delete "loath" and substitute -- path -- therefor.

Signed and Sealed this
Eighth Day of November, 2011

David J. Kappos
*Director of the United States Patent and Trademark Office*